(12) United States Patent
Fischer et al.

(10) Patent No.: US 6,197,992 B1
(45) Date of Patent: Mar. 6, 2001

(54) MONOOLEFINIC $C_5$ MONONITRILES, METHOD FOR THE PRODUCTION AND THE USE THEREOF

(75) Inventors: Jakob Fischer, Kirchdorf; Wolfgang Siegel; Klaus Mundinger, both of Limburgerhof; Gerald Meyer, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/319,877

(22) PCT Filed: Dec. 10, 1997

(86) PCT No.: PCT/EP97/06900

§ 371 Date: Jun. 14, 1999

§ 102(e) Date: Jun. 14, 1999

(87) PCT Pub. No.: WO98/27054

PCT Pub. Date: Jun. 25, 1998

(30) Foreign Application Priority Data

Dec. 16, 1996 (DE) .............................. 196 52 273

(51) Int. Cl.⁷ .................................. C07C 253/00
(52) U.S. Cl. ............................................... 558/338
(58) Field of Search ............................... 558/338

(56) References Cited

U.S. PATENT DOCUMENTS

| | | | |
|---|---|---|---|
| 3,900,526 | 8/1975 | Johnson et al. | 260/681 |
| 4,434,316 | 2/1984 | Barnette | 585/833 |
| 4,493,906 | 1/1985 | Couvillion | 502/346 |
| 4,587,369 | 5/1986 | Cosyns et al. | 585/259 |
| 4,704,492 | 11/1987 | Nemet-Mavrodin | 585/259 |
| 4,831,200 | 5/1989 | Debras et al. | 585/259 |
| 5,484,902 | 1/1996 | Casalnuovo et al. | 536/18 |
| 5,488,129 | 1/1996 | Huser et al. | 558/338 |
| 5,523,453 | 6/1996 | Breikss | 558/338 |
| 5,696,280 | 12/1997 | Shapiro | 558/140 |

FOREIGN PATENT DOCUMENTS

| | | |
|---|---|---|
| 274401 | 7/1988 | (EP) . |
| 315551 | 5/1989 | (EP) . |
| 1161645 | 8/1969 | (GB) . |
| 1424288 | 2/1976 | (GB) . |
| 95/14659 | 6/1995 | (WO) . |
| 95/28228 | 10/1995 | (WO) . |
| 95/30680 | 11/1995 | (WO) . |
| 96/11182 | 4/1996 | (WO) . |

OTHER PUBLICATIONS

Weissermel et al., *J. Ind. Org. Chem.,* 4th Ed, pp. 272–284, 1994.
Huthmacher et al., *App. Hom. Cat. with Org. Comp.,* vol. 1, pp. 465–479 (no date available).
Ullmann's *Enc. of Tech. Chem.,* vol. 1, 3rd ed., 1951, pp. 743–754.

*Primary Examiner*—Joseph K. McKane
*Assistant Examiner*—Joseph Murray
(74) *Attorney, Agent, or Firm*—Keil & Weinkauf

(57) ABSTRACT

The disclosure is a process for preparing mixtures of monoolefinic $C_5$ mononitriles having nonconjugated C=C— and C≡N bonding by catalytic hydrocyanation of a hydrocarbon mixture containing 1,3-butadiene, by first diminishing the proportion of those components in the hydrocarbon mixture which impair the catalytic hydrocyanation and then subjecting the resulting mixture to catalytic hydrocyanation.

14 Claims, No Drawings

MONOOLEFINIC C₅ MONONITRILES, METHOD FOR THE PRODUCTION AND THE USE THEREOF

This Application is a 371 of PCT/EP97/06900 filed Dec. 10, 1997.

DESCRIPTION

The present invention relates to monoolefinic $C_5$ mononitriles in which the C=C bond and the C≡N bond are not conjugated, to a process for their preparation by catalytic hydrocyanation of a 1,3-butadiene-containing hydrocarbon mixture, and to their use as intermediates for further processing to adiponitrile.

The preparation of mixtures of monoolefinic $C_5$ mononitriles which contain, for example, 3-pentenenitrile and 2-methyl-3-butenenitrile from pure 1,3-butadiene is extremely uneconomical, since the latter has to be isolated from industrially obtainable hydrocarbon mixtures by complicated extractive distillation.

1,3-Butadiene-containing hydrocarbon mixtures are obtainable on a large industrial scale. For instance, the processing of petroleum by steam-cracking naphtha gives rise to a hydrocarbon mixture which is known as the $C_4$ cut and which has a high total olefin content, of which about 40% is accounted for by 1,3-butadiene and the remainder by monoolefins and polyunsaturated hydrocarbons and also alkanes. These streams always also contain small proportions of, generally, up to 5% in terms of alkynes, 1,2-dienes and vinylacetylene, which can only be removed by complicated and hence costly processing measures.

One way of removing acetylenes and allenes from diolefin-containing hydrocarbon mixtures consists in partly hydrogenating these mixtures in the presence of catalysts capable of differentiating between these classes of substances. For instance, U.S. Pat. No. 4,587,369 describes selective hydrogenation catalysts based on Pd on an alumina support.

U.S. Pat. No. 4,704,492 describes Cu/Pd catalysts useful as selective hydrogenation catalysts.

For certain uses of the hydrocarbon mixture, it is desirable to minimize the loss of diolefin, for example 1,3-butadiene, while at the same time maximizing the removal of the acetylenes. U.S. Pat. No. 4,493,906 describes a catalyst based on finely divided copper on a $\gamma\text{-Al}_2\text{O}_3$ support with which acetylene is removed virtually completely from a butadiene-containing mixture and the butadiene loss is in the region of not more than 1%.

1,3-Butadiene is for example an important starting material for the production of adiponitrile, from which, for example, α, ω-alkylenediamines can be prepared, an important component for the large scale industrial production of polyamides (nylon). These diamines are generally prepared starting from corresponding dinitriles and subjecting these to a hydrogenation. For instance, all industrially utilized processes for producing 1,6-diaminohexane pass through the intermediate stage of adiponitrile, of which annually about 1.0 million metric tons are produced worldwide. K. Weissermel, H.-J. Arpe, Industrielle Organische Chemie, 4th Edition, VCH Weinheim, pages 266 et seq., describe four fundamentally different routes for the production of adiponitrile:

1. dehydrating amination of adipic acid with ammonia in the liquid or gas phase via the diamide intermediate;
2. indirect hydrocyanation of 1,3-butadiene via the intermediate stage of the 1,4-dichlorobutenes;
3. hydrodimerization of acrylonitrile in an electrochemical process; and
4. direct hydrocyanation of 1,3-butadiene with hydrogen cyanide.

The last process produces in a first stage, by monoaddition, a mixture of isomeric pentenenitriles and methylbutenenitriles, which, in a second stage, is isomerized to predominantly 3- and 4-pentenenitrile. Subsequently, in a third stage, the adiponitrile is formed by anti-Markovnikov hydrogen cyanide addition to 4-pentenenitrile. The reaction takes place in the liquid phase in a solvent, for example tetrahydrofuran, at a temperature within the range from 30 to 150° C. and at atmospheric pressure. Nickel complexes with phosphine or phosphite ligands and metal salt promoters are used as catalysts. The abovementioned review contains no mention of a possible utility of an industrial $C_4$ cut instead of pure 1,3-butadiene as reactant.

Applied Homogeneous Catalysis with Organometallic Compounds, Vol. 1, VCH Weinheim, pages 465 et seq., describes the heterogeneously and homogeneously catalyzed addition of hydrogen cyanide to olefins in general terms. Catalysts used are especially catalysts based on phosphine and phosphite complexes of nickel and palladium which permit a high product selectivity, improved conversions and shortened reaction times. Adiponitrile is prepared by hydrocyanation of butadiene using in the main nickel(0) phosphite catalysts, optionally in the presence of a Lewis acid as promoter. In general, the reaction can be divided into three steps: 1. synthesis of mononitriles by hydrocyanation of 1,3-butadiene; 2. isomerization; 3. synthesis of dinitriles. The monoaddition product is an isomeric mixture of 3-pentenenitrile and 2-methyl-3-butenenitrile, and the selectivity in respect of the linear 3-pentenenitrile is within the range from about 70 to 90%, depending on the catalyst used. If this first reaction step is carried out in the absence of Lewis acids, generally no second addition of hydrogen cyanide takes place and the resulting product mixture can be subjected to an isomerization using the same catalyst systems as in the first reaction step, this time in the presence of a Lewis acid, for example $ZnCl_2$, as promoter. The 2-methyl-3-butenenitrile isomerizes to 3-pentenenitrile on the one hand, and 3-pentenenitrile isomerizes to the various n-cyanonitriles on the other. The cited publication mentions that the thermodynamically most stable isomer, 2-pentenenitrile, in which the C,N triple bond is conjugated with the C,C double bond, inhibits the reaction, since it acts as a catalyst poison. The desired isomerization to 4-pentenenitrile is only possible as a result of the fact that 3-pentenenitrile is isomerized significantly more rapidly to 4-pentenenitrile than to 2-pentenenitrile.

EP-A-0 274 401 describes a process for hydrocyanating pure butadiene using a nickel catalyst containing a mixture of phenyl and m,p-tolyl phosphite ligands.

EP-A-315 551 describes a process for hydrocyanating pure dienes, for example 1,3-butadiene, 1,3-hexadiene, etc., by catalysis with a nickel(0) catalyst which contains an acid as promoter.

U.S. Pat. No. 4,434,316 describes a process for removing the alkenes from a mixture of alkenes and alkanedienes by reacting the mixture with hydrogen cyanide in the presence of a nickel(0) complex as catalyst. The alkadienes react preferentially to form the corresponding nitriles and can be separated from the unconverted alkenes. Such an alkene-alkadiene separation is necessary for example in industrial processes for the production of dinitriles in order that the alkenes, which cannot form dinitriles, can be separated from the alkadienes. The process described is suitable for separating alkenes having 2 to 5 carbon atoms, for example ethylene, propylene, butenes and propenes from alkadienes having 3 to 8 carbon atoms, for example propadiene, butadiene, pentadiene, hexadiene and octadiene. The presence of acetylenically and ethylenically-acetylenically unsaturated hydrocarbons is not considered disadvantageous for the separation process described. The reference does not mention the possibility of hydrocyanating a 1,3-butadiene-containing hydrocarbon mixture and especially a $C_4$ cut from petroleum refineries to produce $C_5$ monoolefin mixtures having a nitrile function.

However, the prior art processes for hydrocyanating 1,3-butadiene-containing hydrocarbon mixtures have the disadvantage that conjugated butenenitriles and/or pentenenitriles are obtained as unwanted by-products. These conjugated butenenitriles and/or pentenenitriles are impossible to separate completely from the nonconjugated products of value, 3-pentenenitrile and 2-methyl-3-butenenitrile, are not further hydrocyanable to adiponitrile and are also pronounced catalyst poisons.

It is an object of the present invention to provide a process for preparing mixtures of monoolefinic $C_5$ mononitriles which is free from the above-described disadvantages and which enables the adiponitrile to be produced economically.

We have found that, surprisingly, this object is achieved by a process of the initially mentioned type by hydrocyanating a 1,3-butadiene-containing hydrocarbon mixture which is essentially free from interfering components, such as alkynes and 1,2-dienes. This is because it was surprisingly found that the above-described disadvantages can be avoided if in particular the proportion of alkynes and 1,2-dienes which form the unwelcome conjugated nitriles on hydrocyanation is reduced in the hydrocarbon hydrocyanation feed mixture. The novel nitrile mixtures prepared according to the invention are therefore especially useful, for example, after further workup and isomerization, as intermediates for the production of adiponitrile by addition of a further equivalent of hydrogen cyanide.

The present invention accordingly provides in a first aspect a process for preparing mixtures of monoolefinic $C_5$ mononitriles having nonconjugated C=C— and C≡N bonding by catalytic hydrocyanation of a hydrocarbon mixture containing 1,3-butadiene, by first diminishing the proportion of those components in the hydrocarbon mixture which impair the catalytic hydrocyanation and then subjecting the resulting mixture to catalytic hydrocyanation.

Components which give rise to catalyst poisons under catalytic hydrocyanation, especially alkynes, 1,2-dienes and mixtures thereof, are partially or completely removed from the hydrocarbon mixture.

Especially the hydrocyanation of a $C_4$ cut which is not completely free from alkynes, for example propyne or butyne, from 1,2-dienes, for example propadiene, and from alkenines, for example vinylacetylene, affords products in which a C=C double bond is conjugated with the C≡N bond. As mentioned above, it is known from Applied Homogeneous Catalysis with organometallic Compounds, Vol. 1, VCH Weinheim, page 479, that the conjugated 2-pentenenitrile formed in the isomerization of 2-methyl-3-butenenitrile and 3-pentenenitrile acts as a reaction inhibitor for the second addition of hydrogen cyanide to form adiponitrile. It was found that the abovementioned conjugated nitriltes obtained on hydrocyanating an unpretreated $C_4$ cut also act as catalyst poisons for the first reaction step of adiponitrile production, the monoaddition of hydrogen cyanide. Direct consequences are a distinctly diminished catalytic activity of the homogeneous nickel catalyst, lower conversions and lower nickel retrieval rates in catalyst recovery. The disadvantages can be avoided, as is shown in the experimental part.

More particularly, selective hydrogenation of the alkyne and 1,2-diene portions according to the invention results in distinctly higher HCN conversions in the hydrocyanation, a distinctly improved nickel balance sheet and better 1,3-butadiene conversions even for a lower 1,3-butadiene excess.

The production of monoolefinic $C_5$ mononitriles according to the process of the invention is preferably carried out using an industrially produced hydrocarbon mixture having a high proportion of 1,3-butadiene. An example of an industrially produced hydrocarbon mixture having a high proportion of 1,3-butadiene is the $C_4$ cut which is obtained in petroleum processing by steam cracking of naphtha and which as a consequence of its method of production always contains alkynes and 1,2-dienes as well. These components are removed by subjecting the $C_4$ cut prior to the addition of hydrogen cyanide to a catalytic partial hydrogenation. This partial hydrogenation takes place in the presence of a hydrogenation catalyst capable of selectively hydrogenating alkynes and 1,2-dienes in the presence of other dienes and monoolefins.

The present process is particularly suitably carried out using, for example, a 1,3-butadiene-enriched mixture ($C_4$ cut), having a 1,3-butadiene content of not less than 10% by volume, preferably not less than 25% by volume, particularly not less than 43% by volume. Preference is given to using a mixture having a very high butadiene content of not less than 35% by volume, preferably not less than 40% by volume, particularly not less than 42% by volume.

An advantageous embodiment of the process of the invention is carried out using an industrially produced $C_4$ cut containing the following hydrocarbons:

10–50% by volume, preferably 25–47% by volume, of 1,3-butadiene;

10–35% by volume, preferably 15–30% by volume, of isobutene;

2–30% by volume, preferably 5–20% by volume, of 1-butene;

1–20% by volume, preferably 3–15% by volume, of n-butane

1–15% by volume, preferably 2–10% by volume, of trans-2-butene;

1–15% by volume, preferably 2–10% by volume, of isobutane;

1–15% by volume, preferably 2–10% by volume, of cis-2-butene and also together about 0.1–5.0% by volume, preferably 0.2–2.5% by volume, of alkynes and 1,2-dienes, for example vinylacetylene, 1-butyne, propyne, propadiene (allene) etc., and trace gases, for example propane, cyclopropane, propene, isopentane, n-pentane, etc., each within the range from about 1 to 500 ppm.

A further advantageous embodiment of the process of the invention is carried out using an industrially produced $C_4$ cut containing the following hydrocarbons:

35–50% by volume, preferably 43–47% by volume, of 1,3-butadiene;

17–35% by volume, preferably 20–30% by volume, of isobutene;

8–18% by volume, preferably 11–15% by volume, of 1-butene;

3–13% by volume, preferably 6–10% by volume, of n-butane

1–7% by volume, preferably 3–5% by volume, of trans-2-butene;

1–5% by volume, preferably 2–4% by volume, of isobutane;
1–5% by volume, preferably 2–5% by volume, of cis-2-butene
and also together about 0.5–1.4% by volume of alkynes and 1,2-dienes, for example vinylacetylene, 1-butyne, propyne, propadiene (allene) etc., and trace gases, for example propane, cyclopropane, propene, isopentane, n-pentane, etc., each within the range from about 5 bis 250 ppm.

The $C_4$ cut is preferably subjected to a selective hydrogenation which catches essentially only the alkynes and 1,2-dienes present. Thus, following the selective hydrogenation, the total proportion of these alkynes and 1,2-dienes in the hydrocarbon is not more than about 1000 ppm, preferably not more than about 800 ppm, especially not more than about 600 ppm. In a specific embodiment, the total post-hydrogenation proportion of these components is not more than 100 ppm. Furthermore, the proportion of 1,3-butadiene especially is diminished only to a small extent, generally by not more than about 10% by volume, preferably by not more than 5% by volume, especially by not more than 1% by volume.

In an advantageous embodiment of the process of the invention, the selective hydrogenation affords a hydrocarbon mixture containing the following hydrocarbons:
10–50% by volume, preferably 25–47% by volume, of 1,3-butadiene;
10–35% by volume, preferably 15–30% by volume, of isobutene;
2–30% by volume, preferably 5–25% by volume, of 1-butene;
1–15% by volume, preferably 2–10% by volume, of trans-2-butene;
1–20% by volume, preferably 3–15% by volume, of n-butane;
1–15% by volume, preferably 2–10% by volume, of cis-2-butene;
1–15% by volume, preferably 2–10% by volume, of isobutane;
and also
10–500 ppm of 1-butyne;
10–1000 ppm of vinylacetylene;
10–250 ppm of propadiene;
5–250 ppm of propyne;
and the abovementioned trace gases each within the range from 5 to 500 ppm.

In a further advantageous embodiment of the process of the invention, the selective hydrogenation affords a hydrocarbon mixture containing the following hydrocarbons:
30–47% by volume, preferably 35–44% by volume, of 1,3-butadiene;
15–35% by volume, preferably 21–30% by volume, of isobutene;
15–25% by volume, preferably 18–22% by volume, of 1-butene;
4–10% by volume, preferably 6–8% by volume, of trans-2-butene;
1.5–7.5% by volume, preferably 3.5–5.5% by volume, of n-butane;
1.5–7.5% by volume, preferably 3.3–5.3% by volume, of cis-2-butene;
0.4–1.4% by volume, preferably 0.7–1.2% by volume, of isobutane;
and also
100–250 ppm of 1-butyne;
80–250 ppm of vinylacetylene;
30–60 ppm of propadiene;
10–50 ppm of propyne;
and the abovementioned trace gases each within the range from 5 to 500 ppm.

Suitable catalysts for the selective hydrogenation are known from the prior art and include customary homogeneous and heterogeneous hydrogenation catalyst systems. The catalysts suitable for the process of the invention are preferably based on a transition metal of the 8th or 1st subgroup, preference being given to using catalysts based on Ni, Pd, Pt, Ru or Cu. Particular preference is given to using catalysts based on Cu or Pd.

Suitable heterogeneous catalyst systems generally comprise one of the aforementioned transition metal compounds on an inert support. Suitable inorganic supports are the customary oxides, especially silicas and aluminas, alumosilicates, zeolites, carbides, nitrides, etc. and mixtures thereof. Preferred supports are $Al_2O_3$, $SiO_2$ and mixtures thereof. The heterogeneous catalysts used in the process of the invention are in particular those described in U.S. Pat. No. 4,587,369; U.S. Pat. No. 4,704,492 and U.S. Pat. No. 4,493,906, which are all fully incorporated herein by reference. Further suitable Cu-based catalyst systems are marketed by Dow Chemical as KLP catalyst.

The addition of hydrogen cyanide to the pretreated, partly hydrogenated $C_4$ cut and specifically to the 1,3-butadiene present therein can be carried out continuously, semicontinuously or batchwise.

The continuous hydrogen cyanide addition comprises formally:
a) feeding the partly hydrogenated $C_4$ cut, hydrogen cyanide and hydrocyanation catalyst into a reactor,
b) reacting the mixture at elevated temperature and elevated pressure,
c) removing from the reacted mixture unconverted hydrogen cyanide and 1,3-butadiene,
d) recycling the gaseous reactor effluent into the reactor optionally after distillative workup,
e) working up the liquid and solid reactor effluent by distillation and recycling the recovered catalyst into the reactor.

Suitable reactors for the continuous reaction are known to the person skilled in the art and are described for example in Ullmann's Encyklopädie der technischen Chemie, Vol. 1, 3rd Edition, 1951, pages 743 et seq. The continuous version of the process of this invention is preferably carried out in a stirred tank battery, preferably a two stage stirred tank battery, or in a tubular reactor. The following is preferably heeded for steps a) to e):

Step a)
The three components of the reaction mixture, hydrogen cyanide, partly hydrogenated $C_4$ cut and catalyst, are generally fed in separate feeds at the rate of their respective consumption. If instead of a homogeneous catalyst, which can be introduced into the reactor for example separately as a solution in a suitable solvent or together with one of the other feeds, a heterogeneous catalyst is used, the latter can also be preinstalled in the reactor in a suitable form.

Step b)
The reaction of the partly hydrogenated $C_4$ cut and specifically the monoaddition of hydrogen cyanide to the 1,3-butadiene present is preferably carried out at elevated temperature and at elevated pressure. The temperature in question is generally within the range from about 20 to about 200° C., preferably within the range from about 70 to about 120° C. The reaction pressure generally is the autogenous pressure of the reaction mixture under the reaction temperatures and is within the range from about 1 to 200 bar, preferably from about 2 to 100 bar, in particular from about 5 to 20 bar.

Step c)

Following the reaction, unconverted 1,3-butadiene and hydrogen cyanide and the other gaseous components present in the reaction mixture are removed from the reaction mixture, separated by distillation and/or recycled (recycle stream). This can be effected in a conventional manner, for example by stripping in a stripping column.

Step d)

Depending on the concentration of unconverted 1,3-butadiene still present, the gaseous effluent can be recycled into the reactor, if necessary after prior distillative workup. To remove residual hydrocyanic acid, the off-gas can be scrubbed with aqueous alkali. Suitable scrubbing liquors include the alkali metal hydroxides, for example KOH and NaOH. The exiting 1,3-butadiene-free $C_4$ mix (raffinate 1) can be subjected to further petrochemical processing.

Step e)

The liquid and/or solid reactor effluent is subjected to a distillative workup to isolate the desired products 3-pentenenitrile and 2-methyl-3-butenenitrile and also to recover the catalyst present. The recovered active catalyst is recycled into the reactor.

An advantageous embodiment of the continuous version of the process comprises using a two stage stirred tank battery in which the residence time per stage is within the range from about 10 to 120 minutes, preferably from about 20 to 60 minutes.

In a further suitable version of the process of this invention, the addition of the hydrogen cyanide to the partly hydrogenated $C_4$ cut is carried out semicontinuously.

The semicontinuous process comprises:
a) filling a pressure-resistant reactor with the partly hydrogenated $C_4$ cut, hydrogen cyanide and a hydrocyanation catalyst and optionally a solvent,
b) reacting the mixture at elevated temperature and elevated pressure and, in semicontinuous operation, feeding in hydrogen cyanide at the rate of its consumption, and
c) reacting to completion and then working up.

Suitable pressure-resistant reactors are known to the person skilled in the art and are described for example in Ullmann's Encyklopädie der technischen Chemie, Vol. 1, 3rd Edition, 1951, pages 769 et seq. In general, the process of the invention is carried out using an autoclave which can be equipped with a stirrer and an internal lining, for example of glass, if desired. The following is preferably heeded for the above steps:

Step a)

The pressure-resistant reactor is charged with the partly hydrogenated $C_4$ cut, hydrogen cyanide, a hydrocyanation catalyst and optionally a solvent before commencement of the reaction. Examples of suitable solvents are aromatic hydrocarbons, such as toluene and xylene, or tetrahydrofuran.

Step b)

The mixture is generally reacted at elevated temperature and elevated pressure. The reaction temperature is generally within the range from about 20 to 200° C., preferably within the range from about 70 to 120° C. The pressure is generally within the range from about 1 to 200 bar, preferably within the range from about 5 to 20 bar. During the reaction, hydrogen cyanide is fed in at the rate of its consumption, and the pressure in the autoclave remains essentially constant. The reaction time is within the range from about 30 minutes to 5 hours, preferably within the range from about 1 hour to 3 hours.

Step c)

To complete the reaction, the reaction time can be followed by a postreaction time of from 0 minutes to about 5 hours, preferably from about 1 hour to 3 hours, during which no further hydrogen cyanide is introduced into the autoclave. The temperature during this period is left essentially constant at the previously set reaction temperature. The workup is carried out according to commonly used processes and comprises removing the unconverted 1,3-butadiene and the unconverted hydrogen cyanide, for example by washing or extraction and the distillative workup of the remaining reaction mixture to remove the products of value and recover still active catalyst.

In a further suitable version of the process of this invention, the addition of the hydrogen cyanide to the partly hydrogenated $C_4$ cut is carried out batchwise. In this case, the reaction conditions described in connection with the semicontinuous processes are essentially observed and no additional hydrogen cyanide is introduced in step b).

Suitable catalysts for the hydrocyanation are known from the prior art and include heterogeneous and preferably homogeneous catalyst systems. In general, catalysts suitable for the process of the invention are based on a transition metal of the 8th subgroup and optionally comprise a metal salt as promoter. The catalyst system used for the monoaddition of hydrogen cyanide preferably contains no addition of promoter.

The process of the invention is preferably carried out using at least one homogeneous catalyst selected from salts or complexes of nickel. Of particular suitability are Ni(0) complexes with phosphine, phosphinite, phosphonite or preferably phosphite ligands. Suitable nickel phosphine, phosphinite, phosphonite or phosphite complexes have the general formula $NiL_4$, where L is $PR_3$, $P(OR)R_2$, $P(OR)_2R$ or $P(OR)_3$ and R is alkyl, cycloalkyl or aryl, preferably phenyl or m,p-tolyl. It is also possible to use mixtures of different radicals R. In a preferred embodiment, the reaction takes place in the presence of an Ni(0) complex which comprises at least one multidentate phosphine, phosphinite, phosphonite or phosphite ligand. Suitable phosphite chelators are described in WO 96/22968, U.S. Pat. No. 5,484,902, WO 96/11182, U.S. Pat. No. 5,523,453, WO 95/30680, WO 95/28228 and WO 95/14659, which are all fully incorporated herein by reference.

The aforementioned catalysts can be used combined with a promoter, if desired. The promoter used is preferably a Lewis acid, for example $AlCl_3$ or $ZnCl_2$. The catalysts used for the monoaddition of hydrogen cyanide preferably contain no addition of a promoter.

In an advantageous embodiment of the process of this invention, one of the aforementioned ligands can be used in excess as solvent. If desired, the 3-pentenenitrile product can also act as solvent.

In general, the production of adiponitrile from a butadiene-containing mixture by addition of 2 mole equivalents of hydrogen cyanide can be divided into three steps:

1. Preparation of $C_5$ monoolefin mixtures having a nitrile function.
2. Isomerization of the 2-methyl-3-butenenitrile in these mixtures to 3-pentenenitrile and isomerization of the resulting 3-pentenenitrile and of the 3-pentenenitrile already present in the mixtures from step 1 to form various n-pentenenitriles. The proportion of 3-pentenenitrile formed should be as high as possible and the proportion of conjugated, catalyst-poisoning 2-pentenenitrile and 2-methyl-2-butenenitrile should be as low as possible.
3. Production of adiponitrile by addition of hydrogen cyanide to the 3-pentenenitrile formed in step 2 and previously isomerized in situ to 4-pentenenitrile.

By-products include for example 2-methylglutaronitrile from the Markovnikov addition of hydrogen cyanide to 4-pentenenitrile or from the anti-Markovnikov addition of hydrogen cyanide to 3-pentenenitrile, and ethylsuccinonitrile from the Markovnikov addition of hydrogen cyanide to 3-pentenenitrile.

The nickel phosphite catalysts preferred for the novel preparation of monoolefinic nitriles in step 1 are advantageously also suitable for the position and double bond isomerization in step 2 and the second addition of hydrogen cyanide in step 3. A suitable procedure involves for example the monoaddition of step 1 being carried out in the absence of promoters, for example Lewis acids such as $ZnCl_2$, the isomerization of step 2 being carried out in the presence of Lewis acids, to optimize the yield of 3-pentenenitrile, and the second addition in step 3 being optionally carried out with the $ZnCl_2$ having been replaced by triphenylboron to optimize the adiponitrile selectivity of the reaction.

The novel process for preparing monoolefinic $C_5$ nitriles from an essentially alkyne- and 1,2-diene-free hydrocarbon mixture makes it possible to achieve higher hydrogen cyanide conversions and higher 1,3-butadiene conversions than in the hydrocyanation of an unpretreated $C_4$ cut. The hydrogen cyanide conversions achieved are not less than 90%, preferably not less than 95%, particularly preferably not less than 98%, especially not less than 99%. The semicontinuous process produces under otherwise identical reaction conditions distinctly lower hydrogen cyanide conversions with unpretreated $C_4$ cut.

The industrially preferred continuous form of the process of the invention affords hydrogen cyanide conversions in the region of about 98% for unpretreated $C_4$ cut under reaction conditions which are otherwise identical to those of the process of this invention compared with essentially complete conversions in the region of, for example, 99.8% on use of $C_4$ cut pretreated according to the invention. Since the continuous process is carried out with recycling of the active nickel catalyst, and the catalyst is added to the reaction mixture only in small amounts, even a slight hydrogen cyanide excess due to incomplete conversion has a strongly adverse effect on the nickel balance of the reaction. Thus, the continuous process of the invention surprisingly has a higher catalyst recycling rate and so longer catalyst on-stream times than known processes. This is also relevant from ecological aspects, since the nickel cyanide formed from the active catalyst and hydrogen cyanide is highly toxic and has to be expensively worked up or disposed of.

If, according to the process of this invention, an above-described partly hydrogenated $C_4$ cut is subjected to a hydrocyanation, essentially only the 1,3-butadiene is monohydrocyanated. According to gas space analyses, the monoolefins present in the pretreated $C_4$ cut do not react with hydrogen cyanide but are isomerized in some instances. For instance, the 1-butene component is observed to isomerize to cis-and trans-2-butene. The product mixture obtained generally comprises isomeric pentenenitriles and methylbutenenitriles, such as 3-pentenenitrile, 2-pentenenitrile, 4-pentenenitrile, 2-methyl-2-butenenitrile, 2-methyl-3-butenenitrile, etc.

It is preferable to obtain a high proportion of 4-pentenenitrile and also of products which are isomerizable to 4-pentenenitrile, such as 3-pentenenitrile and 2-methyl-3-butenenitrile. Furthermore, the proportion of conjugated 2-pentenenitrile, which acts as a catalyst poison, is low and is preferably below 1% by weight, especially within the range from about 0.1 to 0.2% by weight, based on $C_4$ cut used.

The product ratio of 3-pentenenitrile to 2-methyl-3-butenenitrile is generally within the range from about 1.5:1 to 2.5:1, preferably within the range from 1.8:1 to 2.3:1.

As gas space analyses show, if $C_4$ cut is used for the hydrocyanation which has not been partly hydrogenated, it is not only 1,3-butadiene which is hydrocyanated, but also the alkynes and 1,2-dienes present, to form products having a C,C double bond conjugated with the nitrile function. Owing to the effect of these compounds as catalyst poisons, the nickel retrieval rates and the catalyst on-stream times are lower than in the process of the invention. Lower catalyst activities lead to lower conversions.

The present invention further provides the monoolefinic $C_5$ mononitriles available by the process of the invention.

The invention further provides a process for selective hydrogenation of $C_4$ cuts, which comprises reacting a 1,3-butadiene-containing hydrocarbon mixture which additionally includes at least one alkyne and/or 1,2-diene with hydrogen in the presence of a hydrogenation catalyst.

The present invention further provides a selectively hydrogenated $C_4$ cut having a total content of alkynes and 1,2-dienes of not more than 1000 ppm, preferably not more than 800 ppm, in particular not more than 600 ppm, especially not more than 100 ppm.

The present invention further provides a process for preparing adiponitrile, which comprises catalytically hydrocyanating a $C_5$ mononitrile mixture prepared as described above, optionally after further workup or isomerization.

The Examples which follow illustrate the invention.

EXAMPLES

The examples which follow were carried out using a partly hydrogenated hydrocarbon mixture containing:
38.9% by volume of 1,3-butadiene,
22.4% by volume of isobutene,
19.8% by volume of 1-butene,
4.5% by volume of n-butane,
7.05% by volume of trans-2-butene,
0.89% by volume of isobutane,
4.30% by volume of cis-2-butene,
159 ppm of vinylacetylene,
214 ppm of 1-butyne,
29 ppm of propyne,
44 ppm of propadiene,
156 ppm of i-pentane,
45 ppm of cyclopropane
333 ppm of propene,
6 ppm of n-pentane,
6 ppm of propane The comparative examples which follow were carried out using an unhydrogenated hydrocarbon mixture containing:
45.2% by volume of 1,3-butadiene,
22.0% by volume of isobutene,
12.7% by volume of 1-butene,
8.2% by volume of n-butane,
3.8% by volume of trans-2-butene,
2.92% by volume of isobutane,
2.64% by volume of cis-2-butene,
0.621% by volume of vinylacetylene,
0.128% by volume of 1-butyne,
671 ppm of propyne,
357 ppm of propadiene,
258 ppm of i-pentane,
86 ppm of cyclopropane
23 ppm of propene,
15 ppm of n-pentane,
6 ppm of propane

Example 1
Continuous Hydrocyanation of Partly Hydrogenated $C_4$ Cut
Catalyst Composition
25% by weight of tetrakis(tri-m/p-tolyl phosphite) nickel(0)
60% by weight of tri-m/p-tolyl phosphite
15% by weight of 3-pentenenitrile/2-methyl-3-butenenitrile.

Partly hydrogenated $C_4$ cut, catalyst solution and hydrogen cyanide are introduced into a two stage stirred tank battery (pressure: 15 bar, temperature of reactor 1: 102° C., temperature of reactor 2: 95° C., residence time: 40 min/reactor). The effluent is stripped free from hydrocyanic acid and butadiene, the gas space is analyzed, and the gaseous effluent is passed through an NaOH scrubbing tower. Liquid/solid effluents are analyzed, worked up by distillation to remove the products of value and recover still active catalyst, and the products thus obtained are again analyzed. The HCN conversions are determined by volumetric analysis of the reactor solutions from the two reactors. The nickel retrieval rate (recovery of active catalyst) is determined by means of elemental analysis.

Gas space analysis shows 1,3-butadiene to be hydrocyanated selectively; 1-butene is isomerized to cis- and trans-2-butene. The relative percentage proportion of i-butene, i-butane and n-butane remains the same before and after the reaction, within 10 the margin of measuring error. The results are summarized in Table 1.

Comparative Example 1
Continuous Hydrocyanation of Unhydrogenated $C_4$ Cut An unhydrogenated hydrocarbon mixture of the above-specified composition is reacted similarly to Example 1. The results are likewise reproduced in Table 1.

Comparative Example 2
Continuous Hydrocyanation of Unhydrogenated $C_4$ Cut An unhydrogenated hydrocarbon mixture of the above-specified composition is reacted similarly to Example 1, except that the catalyst feed is raised from 2.72 mmol/h to 4.85 mmol/h. The results are likewise reproduced in Table 1.

TABLE 1

Continuous hydrocyanation of partly hydrogenated and unhydrogenated $C_4$ cuts

| | | Ex. 1 | Comp. Ex. 1 | Comp. Ex. 2 |
|---|---|---|---|---|
| Feeds | Ni cat. [mmol/h] | 2.76 | 2.72 | 4.85 |
| | 1,3-Butadiene (as $C_4$ cut) [mmol/h] | 483 | 533 | 513 |
| | HCN [mmol/h] | 414 | 421 | 455 |
| Weight ratios [% by weight] | Butadiene:HCN | 1.17:1 | 1.27:1 | 1.13:1 |
| | Ni:ligand | 1:14 | 1:14 | 1:14 |
| | Turnover number | 151 | 154 | 94 |
| | Butadiene selectivity [%] | 98 | 97 | 97 |
| | Product ratio of 3-PN:2-M-3BN[1] [% by weight] | 2.0:1 | 1.95:1 | 2.1:1 |
| Recovered act. cat. quantity of Ni [% by weight] | | 89.0 78.0 90.0 | 66.0 61.0 61.3 | 80.5 72.1 65.3 |
| Conversion | HCN [% by weight] | >99.8 | 98.0 | 99.0 |

[1]) 3-PN = 3-pentenenitrile, 2-M-3-BN = 2-methyl-3-butenenitrile

As Example 1 and Comparative Examples 1 and 2 clearly show, the hydrogen cyanide conversion on using a selectively hydrogenated hydrocarbon mixture is higher than with an unpretreated mixture. Furthermore, Example 1 gives distinctly higher nickel retrieval rates than the comparative examples. The butadiene selectivity is about 1% higher in the process of the invention than in the reference process. Example 1 has less butadiene (excess component) than Comparative Examples 1 and 2. Nonetheless, the conversion of HCN (deficient component) is higher. This effect is surprising, because the conversion of the deficient component should have increased with increasing amount of excess component. Comparative Example 2, which utilizes a distinctly higher catalyst content, still does not match the results of Example 1.

Example 2
Semicontinuous Hydrocyanation of Partly Hydrogenated $C_4$ Cut
40 g of toluene,
20.3 g of prehydrogenated $C_4$ cut (=7.9 g of 1,3-butadiene),
4.7 g of catalyst composition containing:
   25% by weight of tetrakis(tri-m/p-tolyl phosphite) nickel (0)
   60% by weight of tri-m/p-tolyl phosphite
   15% by weight of 3-pentenenitrile,
are introduced into a glass-lined autoclave and heated at 90° C. for 2 h. During this time, 3.2 g of HCN and 40 g of toluene are metered in. The mixture is then left to react at 90° C. for 2 h.

Conversion rate (according to volumetric analysis of unconverted HCN): 98.0%
Yield (according to integration of gas chromatogram): 98.8% based on HCN

Example 3
Semi-continuous hydrocyanation of a partially hydrogenated $C_4$ cut using tri(m/p-tolyl)phosphite A glass autoclave is charged with 20.3 g of partially hydrogenated $C_4$ cut (corresponding to 7.9 g (0.14 mol) of 1,3-butadiene), 2.75 g of a mixed catalyst (composition: 0.69 g (0.468 mmol) of tetrakis(tri-m/p-tolylphosphite) nickel(0), 1.65 g (4.68 mmol) of tri-m/p-tolylphosphite and 0.41 g 3-pentene nitrile) and 40 g of toluene at room temperature and heated to 90 ° C., the initial pressure being 4.4 bar. A mixture of 3.2 g (0.117 mol) of freshly distilled hydrogen cyanide in 40 g of toluene is continuously metered in over a period of 100 minutes, whereupon the pressure drops to 3.1 bar. The reaction is then completed by further reacting at 90° C. for another 120 minutes. The course of the reaction is monitored by pressure and temperature measurements. After cooling off, the liquid reaction product is analyzed.

Conversion rate (as determined by volumetric analysis of unreacted HCN): 97.6%
GC-analysis (column: 30 m stabil-wax, temperature settings: 5 minutes isothermally at 50° C., then heating to 240°

C. at a rate of 5° C./min, gas chromatograph: Hewlett Packard HP-5890), with internal standard (benzonitrile): 96.8% 3-pentene nitrile and 2-methyl-3-butene nitrile, based on initial hydrogen cyanide. Ratio 3-pentene nitrile: 2-methyl-3-butene nitrile=1.64:1.

Example 4

Semi-Continuous Hydrocyanation of a Partially Hydrogenated $C_4$ Cut Using Ligand A Ligand A

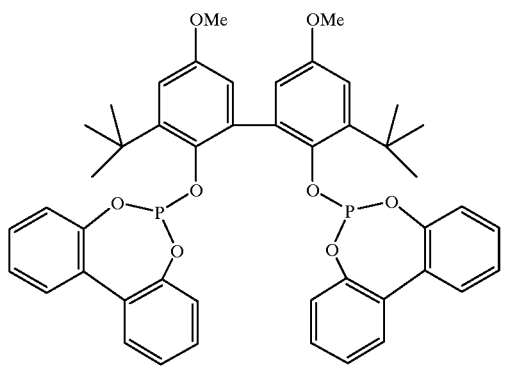

The preparation of ligand A is disclosed in WO 95/14 659 and in the references cited therein.

In a glass autoclave, 0.41 g (1.5 mmol) of Bis(1,5-cyclooctadiene)nickel(0), 0.44 g of ligand A and 10 g of toluene are mixed. Then, a mixture of 20.8 g of partially hydrogenated $C_4$ cut (corresponding to 8.1 g (0.15 mol) of 1,3-butadiene) in 40 g of toluene is added. The glass autoclave is tightly sealed and the reaction mixture is heated to 80° C., the initial pressure being 3.1 bar. A mixture of 4.0 g (0.15 mol) of freshly distilled hydrogen cyanide in 40 g of toluene is continuously metered in over a period of 120 minutes, whereupon the pressure drops to 1.5 bar. The reaction is then completed by further reacting at 80° C. for another 120 minutes. The course of the reaction is monitored by pressure and temperature measurements. After cooling off, the liquid reaction product is analyzed.

Conversion rate (as determined by volumetric analysis of unreacted HCN): 88.7%

GC-analysis (column: 30 m stabil-wax, temperature settings: 5 minutes isothermally at 50° C., then heating to 240° C. at a rate of 5° C./min, gas chromatograph: Hewlett Packard HP-5890), with internal standard (benzonitrile): 89.3% 3-pentene nitrile and 2-methyl-3-butene nitrile, based on initial hydrogen cyanide.

Ratio 3-pentene nitrile: 2-methyl-3-butene nitrile =0.27:1.

Example 5

Semi-Continuous Hydrocyanation of a Partially Hydrogenated $C_4$ Cut Using Ligand B Ligand B

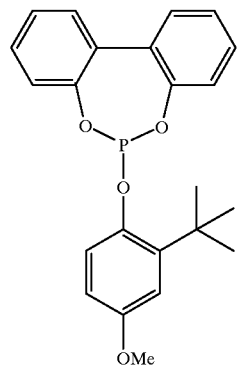

The preparation of ligand B is disclosed in WO 95/29 153. In a glass autoclave, 0.41 g (1.5 mmol) of Bis(1,5-cyclooctadiene)nickel(0), 2.36 g (6 mmol) of ligand B and 10 g of toluene are mixed. Then, a mixture of 20.8 g of partially hydrogenated $C_4$ cut (corresponding to 8.1 g (0.15 mol) of 1,3-butadiene) in 40 g of toluene is added. The glass autoclave is tightly sealed and the reaction mixture is heated to 80° C., the initial pressure being 3.1 bar. A mixture of 4.0 g (0.15 mol) of freshly distilled hydrogen cyanide in 40 g of toluene is continuously metered in over a period of 100 minutes, whereupon the pressure drops to 2.1 bar. The reaction is then completed by further reacting at 80° C. for another 140 minutes. The course of the reaction is monitored by pressure and temperature measurements. After cooling off, the liquid reaction product is analyzed.

Conversion rate (as determined by volumetric analysis of unreacted HCN): 81.3%

GC-analysis (column: 30 m stabil-wax, temperature settings: 5 minutes isothermally at 50° C., then heating to 240° C. at a rate of 5° C./min, gas chromatograph: Hewlett Packard HP-5890), with internal standard (benzonitrile): 81.9% 3-pentene nitrile and 2-methyl-3-butene nitrile, based on initial hydrogen cyanide. Ratio 3-pentene nitrile : 2-methyl-3-butene nitrile =1.24:1.

The differences between the conversion rates determined by volumetric analysis and by gas chromatography are within the accuracy of measurement of the two methods.

We claim:

1. A process for preparing mixtures of monoolefinic $C_5$ mononitriles having nonconjugated C=C and C≡N bonding by catalytic hydrocyanation of a hydrocarbon mixture containing 1,3-butadiene, wherein the hydrocarbon mixture is reacted with hydrogen in the presence of a hydrogenation catalyst capable of hydrogenating alkynes and 1,2-dienes with high selectivity without significantly diminishing the 1,3-butadiene content in order to remove alkynes, 1,2-dienes and mixtures thereof partially or completely so that the proportion of those components in the hydrocarbon mixture which impair the catalytic hydrocyanation is diminished and then subjecting the resulting mixture to catalytic hydrocyanation.

2. The process of claim 1, wherein the hydrocarbon mixture used has a 1,3-butadiene content of at least 10% by volume.

3. The process of claim 1, wherein the 1,3-butadiene-containing hydrocarbon mixture used is a $C_4$ cut from petroleum processing.

4. The process of claim 1, wherein the hydrocarbon mixture used comprises from 10 to 50% by volume of 1,3-butadiene and also in total from about 0.1 to 5% by volume of alkynes and/or 1,2-dienes.

5. The process of claim 1, wherein the hydrocyanation catalyst catalyzes the position isomerization and double bond isomerization of the hydrocarbon mixture and/or of the nitriles as well as the hydrogen cyanide addition.

6. The process of claim 1, wherein the product mixture obtained comprises isomeric pentenenitriles and methylbutenenitriles.

7. A process for preparing adiponitrile, which comprises catalytically hydrocyanating a $C_5$ mononitrile mixture prepared as claimed in any of claims 1 to 6, optionally after further workup or isomerization.

8. The process of claim 2 wherein the 1,3-butadiene content is at least 25% by volume.

9. The process of claim 8 wherein the 1,3-butadiene content is at least 40% by volume.

10. The process of claim 4 wherein the 1,3-butadiene content is from 25 to 47% by volume and the alkyne and/or 1,2-diene content is from 0.2 to 2.5% by volume.

11. The process of claim 6, wherein the product mixture obtained comprises 3-pentenenitrile, 2-pentenenitrile, 4-pentenenitrile, 2-methyl-2-butenenitrile, 2-methyl-3-butenenitrile or mixtures thereof as the isomeric pentenenitriles and methylbutenenitriles.

12. The process of claim 1 wherein the alkynes and 1,2-dienes are partially removed from the hydrocarbon mixture during the hydrogenation step.

13. The process of claim 1 wherein the selective hydrogenation affords a hydrocarbon mixture containing a total content of alkynes and 1,2-dienes within the range of about 100 to 1000 ppm.

14. The process of claim 1 wherein the selective hydrogenation affords a hydrocarbon mixture containing:

10–500 ppm of 1-butyne;

10–1000 ppm of vinylacetylene;

10–250 ppm of propadiene; and

10–250 ppm of propyne.

* * * * *

UNITED STATES PATENT AND TRADEMARK OFFICE
CERTIFICATE OF CORRECTION

PATENT NO. : 6,197,992 B1
DATED : March 6, 2001
INVENTOR(S) : Fischer et al.

It is certified that error appears in the above-identified patent and that said Letters Patent is hereby corrected as shown below:

<u>Column 16, claim 14,</u>
Line 17, "10-250 ppm of propyne" should be -- 5-250 ppm of propyne --.

Signed and Sealed this

Eleventh Day of September, 2001

Attest:

*Nicholas P. Godici*

NICHOLAS P. GODICI
*Attesting Officer*    *Acting Director of the United States Patent and Trademark Office*